US011964035B2

(12) United States Patent
Baldwin et al.

(10) Patent No.: US 11,964,035 B2
(45) Date of Patent: *Apr. 23, 2024

(54) WHIPPED GEL FORMULATIONS

(71) Applicants: BEIERSDORF AG, Hamburg (DE); Formulated Solutions, LLC, Largo, FL (US)

(72) Inventors: Stephen Baldwin, Flanders, NJ (US); Nanhye Kim, New Providence, NJ (US); Tom Meyer, Germantown, TN (US); Eric Dann, Safety Harbor, FL (US); Thomas Dann, Palm Harbor, FL (US); Renee Nelson, Brandon, FL (US); Brian Dann, Clearwater, FL (US); Anna Erixon, Lander, WY (US)

(73) Assignees: BEIERSDORF AG, Hamburg (DE); Formulated Solutions, LLC, Largo, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/300,342

(22) PCT Filed: May 11, 2017

(86) PCT No.: PCT/US2017/032281
§ 371 (c)(1),
(2) Date: Nov. 9, 2018

(87) PCT Pub. No.: WO2017/197196
PCT Pub. Date: Nov. 16, 2017

(65) Prior Publication Data
US 2019/0142709 A1  May 16, 2019

Related U.S. Application Data

(60) Provisional application No. 62/396,431, filed on Sep. 19, 2016, provisional application No. 62/334,880, filed on May 11, 2016.

(51) Int. Cl.
| | | |
|---|---|---|
| A61K 8/04 | (2006.01) | |
| A23P 30/40 | (2016.01) | |
| A61K 8/19 | (2006.01) | |
| A61K 8/25 | (2006.01) | |
| A61K 8/31 | (2006.01) | |
| A61K 8/34 | (2006.01) | |
| A61K 8/35 | (2006.01) | |
| A61K 8/40 | (2006.01) | |
| A61K 8/44 | (2006.01) | |
| A61K 8/49 | (2006.01) | |
| A61K 8/58 | (2006.01) | |
| A61K 8/73 | (2006.01) | |
| A61K 8/81 | (2006.01) | |
| A61K 8/892 | (2006.01) | |

(Continued)

(52) U.S. Cl.
CPC .............. *A61K 8/046* (2013.01); *A23P 30/40* (2016.08); *A61K 8/042* (2013.01); *A61K 8/19* (2013.01); *A61K 8/25* (2013.01); *A61K 8/31* (2013.01); *A61K 8/34* (2013.01); *A61K 8/342* (2013.01); *A61K 8/345* (2013.01); *A61K 8/347* (2013.01); *A61K 8/35* (2013.01); *A61K 8/40* (2013.01); *A61K 8/44* (2013.01); *A61K 8/498* (2013.01); *A61K 8/58* (2013.01); *A61K 8/731* (2013.01); *A61K 8/8152* (2013.01); *A61K 8/8182* (2013.01); *A61K 8/892* (2013.01); *A61K 8/922* (2013.01); *A61K 9/0014* (2013.01); *A61K 9/06* (2013.01); *A61K 47/02* (2013.01); *A61K 47/10* (2013.01); *A61K 47/44* (2013.01); *A61Q 5/06* (2013.01); *A61Q 7/00* (2013.01); *A61Q 11/00* (2013.01); *A61Q 17/04* (2013.01); *A61Q 19/004* (2013.01); *B65D 83/752* (2013.01); *A61K 2800/22* (2013.01); *A61K 2800/524* (2013.01); *A61K 2800/87* (2013.01)

(58) Field of Classification Search
CPC ............... A61K 8/37; A61Q 5/00; A61Q 5/12
USPC .......................................................... 424/401
See application file for complete search history.

(56) References Cited

U.S. PATENT DOCUMENTS

| | | |
|---|---|---|
| 3,395,215 A | 7/1968 | Schubert et al. |
| 3,710,538 A | 1/1973 | Lowy |

(Continued)

FOREIGN PATENT DOCUMENTS

| | | |
|---|---|---|
| AU | 2017263531 A1 | 10/2018 |
| AU | 2017263533 A1 | 10/2018 |

(Continued)

OTHER PUBLICATIONS

Dailymed, "Coppertone Defend and Care Oil Free Lotion SPF 30." www.dailymed.nlm.nih.gov. Published online Dec. 17, 2015 (Year: 2015).*

(Continued)

*Primary Examiner* — Walter E Webb
(74) *Attorney, Agent, or Firm* — Liang & Hennessey LLP; Stanley D. Liang (57) ABSTRACT

The present disclosure relates to, inter alia, a gel formulation in a package, the package may be pressurized. The formulation comprises one or more active agents and is co-mingled with a gas propellant prior to being filled under pressure into the package. The gas propellant is added in sufficient amounts to be dispersed in the formulation; the pressurized package is under sufficient pressure suitable to maintain the first gas propellant dispersed in the formulation. The pressurized package is under sufficient pressure to expel the formulation as a whipped gel formulation upon application of external force on the formulation in the package. The present disclosure also relates to, inter alia, a method of preparing the disclosed formulation; a package comprising the disclosed formulation, and a method of using the disclosed formulation.

12 Claims, 2 Drawing Sheets

(51) Int. Cl.
*A61K 8/92* (2006.01)
*A61K 9/00* (2006.01)
*A61K 9/06* (2006.01)
*A61K 47/02* (2006.01)
*A61K 47/10* (2017.01)
*A61K 47/44* (2017.01)
*A61Q 5/06* (2006.01)
*A61Q 7/00* (2006.01)
*A61Q 11/00* (2006.01)
*A61Q 17/04* (2006.01)
*A61Q 19/00* (2006.01)
*B65D 83/14* (2006.01)

(56) References Cited

U.S. PATENT DOCUMENTS

| | | | |
|---|---|---|---|
| 3,970,584 | A | 7/1976 | Hart et al. |
| 4,670,272 | A | 6/1987 | Chen et al. |
| 4,777,041 | A | 10/1988 | Mercado |
| 5,104,987 | A | 4/1992 | King |
| 5,214,925 | A | 6/1993 | Hoy et al. |
| 5,560,859 | A | 10/1996 | Hartmann et al. |
| 5,858,343 | A | 1/1999 | Szymczak |
| 6,322,776 | B1* | 11/2001 | Ortega, II .............. A61K 8/34 424/401 |
| 7,070,722 | B1* | 7/2006 | Gilchrist .............. A61K 9/122 156/305 |
| 2004/0052826 | A1* | 3/2004 | Fernandez-Kleinlein .............. A61K 31/00 424/401 |
| 2004/0170586 | A1 | 9/2004 | Ferrari et al. |
| 2004/0197270 | A1 | 10/2004 | Mundschenk |
| 2004/0241099 | A1 | 12/2004 | Popp et al. |
| 2004/0247534 | A1 | 12/2004 | Stoltz |
| 2004/0258627 | A1 | 12/2004 | Riedel et al. |
| 2004/0258628 | A1 | 12/2004 | Riedel et al. |
| 2005/0053632 | A1 | 3/2005 | Schafer et al. |
| 2005/0079142 | A1 | 4/2005 | Brunckhorst et al. |
| 2008/0017671 | A1* | 1/2008 | Shieh .............. B65D 83/752 222/394 |
| 2008/0138296 | A1 | 6/2008 | Tamarkin et al. |
| 2008/0253973 | A1 | 10/2008 | Tamarkin et al. |
| 2008/0260655 | A1 | 10/2008 | Tamarkin et al. |
| 2010/0266649 | A1 | 10/2010 | Maitra et al. |
| 2011/0281827 | A1 | 11/2011 | Tamarkin et al. |
| 2012/0065163 | A1 | 3/2012 | Zhao |
| 2012/0087872 | A1 | 4/2012 | Tamarkin et al. |
| 2012/0213712 | A1 | 8/2012 | Kasai et al. |
| 2012/0288462 | A1 | 11/2012 | Lebok et al. |
| 2012/0288465 | A1 | 11/2012 | Loechel |
| 2012/0301422 | A1 | 11/2012 | Meyer |
| 2013/0011341 | A1 | 1/2013 | Nguyen et al. |
| 2013/0233310 | A1 | 9/2013 | Hilgers et al. |
| 2014/0030198 | A1* | 1/2014 | Fares .............. A61K 8/40 424/59 |
| 2014/0079648 | A1 | 3/2014 | Cohen |
| 2014/0120039 | A1 | 5/2014 | Baldwin et al. |
| 2014/0131395 | A1 | 5/2014 | Chang |
| 2016/0101051 | A1* | 4/2016 | Tamarkin .............. A61K 31/58 424/45 |
| 2019/0142709 | A1 | 5/2019 | Baldwin et al. |
| 2019/0151207 | A1 | 5/2019 | Baldwin et al. |
| 2019/0282463 | A1 | 9/2019 | Baldwin et al. |
| 2019/0282464 | A1 | 9/2019 | Baldwin et al. |
| 2019/0367256 | A1 | 12/2019 | Baldwin et al. |

FOREIGN PATENT DOCUMENTS

| | | |
|---|---|---|
| CN | 1217650 A | 5/1999 |
| CN | 1713891 A | 12/2005 |
| CN | 103547247 A | 1/2014 |
| CN | 110035737 A | 7/2019 |
| DE | 10229812 A1 | 1/2004 |
| DE | 10304721 A1 | 8/2004 |
| EP | 1391192 A1 | 2/2004 |
| EP | 1508326 A1 | 2/2005 |
| EP | 2319586 A1 | 5/2011 |
| EP | 2636401 A1 | 9/2013 |
| EP | 3454662 A1 | 3/2019 |
| EP | 3454826 A1 | 3/2019 |
| EP | 3454946 A1 | 3/2019 |
| EP | 3454949 A1 | 3/2019 |
| ES | 2560540 * | 6/2016 ............... A61K 9/00 |
| JP | H0625051 B2 | 2/1994 |
| WO | WO200103663 * | 1/2001 ............... A61K 7/42 |
| WO | 2004022019 A1 | 3/2004 |
| WO | 2005007516 A2 | 1/2005 |
| WO | 2012154918 A2 | 11/2012 |
| WO | 2017112727 A1 | 6/2017 |
| WO | 2017197193 A1 | 11/2017 |
| WO | 2017197194 A1 | 11/2017 |
| WO | 2017197195 A1 | 11/2017 |
| WO | 2017197196 A1 | 11/2017 |
| WO | 2017197202 A1 | 11/2017 |

OTHER PUBLICATIONS

International Search Report and Written Opinion received in PCT/US2017/032292 dated Jul. 26, 2017, pp. 10.

International Preliminary Report received in PCT/US2017/032292 dated Nov. 13, 2018, pp. 7.

Aurena Laboratories "SunScreen Bag on Valve", Retrieved from the Internet, Nov. 19, 2014, pp. 6.

International Search Report and Written Opinion received in PCT/US2017/032277 dated Aug. 1, 2017, pp. 15.

International Preliminary Report received in PCT/US2017/032277 dated Nov. 13, 2018, pp. 10.

International Search Report and Written Opinion received in PCT/US2017/032278 dated Jul. 26, 2017, pp. 9.

International Preliminary Report received in PCT/US2017/032278 dated Nov. 13, 2018, pp. 6.

Mintel, "Hair Styling Foam", Oct. 2013, XP002772098, Online.

Mintel, "Pack Facial Mask", Mar. 2016, XP002772099, Online.

Mintel, "Body Whip Moisture Cream", Jul. 2008, XP002772100, Online.

Mintel, "Body Whip Cream", Aug. 2009, XP002772101, Online.

International Search Report and Written Opinion received in PCT/US2017/032279 dated Jul. 28, 2017, pp. 11.

International Preliminary Report received in PCT/US2017/032279 dated Nov. 13, 2018, pp. 8.

International Search Report and Written Opinion received in PCT/US2017/032281 dated Aug. 1, 2017, pp. 16.

International Preliminary Report received in PCT/US2017/032281 dated Nov. 13, 2018, pp. 11.

Australia IP, Examination report No. 1 for standard patent application for Australian App. No. 2017263538 (dated Feb. 25, 2021).

USPTO, Non-Final Rejection of the U.S. Exam Report for U.S. Appl. No. 16/300,270 (dated Jul. 23, 2020).

USPTO, Non-Final Rejection of the U.S. Exam Report on U.S. Appl. No. 16/300,245 (dated Feb. 5, 2021).

CIPO, Examination Report and Examination Search Report for Canadian App. No. 3,023,714 (dated Mar. 1, 2021).

EPO, Communication pursuant to Article 94(3) EPC for European App. No. 17726753.1.

Australia IP, Examination report No. 1 for standard patent application for Australian App. No. 2017263531 (dated Feb. 25, 2021).

USPTO, Non-Final Rejection of the U.S. Exam Report on U.S. Appl. No. 16/300,245 (dated Jul. 23, 2020).

USPTO, Final Rejection of the U.S. Exam Report on U.S. Appl. No. 16/300,323 (dated Nov. 18, 2020).

CIPO, Examination Report and Examination Search Report for Canadian App. No. 3,023,669 (dated Jan. 29, 2021).

Australia IP, Examination report No. 1 for standard patent application for Australian App. No. 2017263532 (dated Feb. 25, 2021).

CIPO, Examination Report and Examination Search Report for Canadian App. No. 3,023,680 (dated Feb. 17, 2021).

(56) References Cited

OTHER PUBLICATIONS

EPO, Communication pursuant to Article 94(3) EPC for European App. No. 17725450.5 (dated Mar. 19, 2021).
Australia IP, Examination report No. 1 for standard patent application for Australian App. No. 2017263533 (dated Feb. 25, 2021).
USPTO, Non-Final Rejection of the U.S. Exam Report on U.S. Appl. No. 16/300,323 (dated Jun. 12, 2020).
CIPO, Examination Report and Examination Search Report for Canadian App. No. 3,023,702 (dated Feb. 1, 2021).
EPO, Communication pursuant to Article 94(3) EPC for European App. No. 17726754.9 (dated Feb. 23, 2021).
Australia IP, Examination report No. 1 for standard patent application for Australian App. No. 2017263534 (dated Feb. 25, 2021).
USPTO, Non-Final Rejection of the U.S. Exam Report on U.S. Appl. No. 16/300,289 (dated Feb. 5, 2021).
CIPO, Examination Report and Examination Search Report for Canadian App. No. 3,023,703 (dated Feb. 12, 2021).
EPO, Communication pursuant to Article 94(3) EPC for European App. No. 17726162.5 (dated Apr. 2, 2021).
EPO, Communication pursuant to Article 94(3) EPC for European App. No. 17725453.9 (dated Mar. 19, 2021).
USPTO, Non-Final Rejection of the U.S. Exam Report on U.S. Appl. No. 16/300,289 (dated Jul. 27, 2020).
USPTO, Non-Final Rejection of the U.S. Exam Report on U.S. Appl. No. 16/300,270 (dated Feb. 5, 2021).
USPTO, Non-Final Rejection of the U.S. Exam Report on U.S. Appl. No. 16/300,270 (dated Jul. 23, 2020).
Mexican Patent Office, Mexican Official Action for Mexican App. No. MX/a/2018/013754 (dated Jun. 22, 2021), pp. 1-6.
Food Crumbles, The Science of Foams in Food, Apr. 5, 2020, https://foodcrumbles.com/science-of-foams-in-food (Year 2020), 14 pgs.
Coppertone Sport SPF 15, https://dailymed.nlm.nih.gov/dailymed/lookup.cfm?setid=27f80779-1b01-7522e054-00144ff8d46c,hereafter Coppertone), accessed Jan. 15, 2021. (Year: 2015) 6 pages.
International Application No. PCT/US2018/032184, International Search Report dated Jul. 25, 2018, 5 pages.
Mintel, "Dry Touch Oil Free Sunscreen Spray SPF 50" Online, 2016, XP002783084, 11 pages.
Mintel, "High Performance Sunscreen SPF 50", Online, 2016, XP002783085, 9 pages.
USPTO, Non-Final Rejection of the U.S. Exam Report on U.S. Appl. No. 16/612,114 (dated May 13, 2021), 18 pages.
Chinese Office Action received in 201880031248.0, dated Apr. 18, 2022, pp. 6.
Chinese Office Action received in Chinese Application No. 201780028415.1 dated Dec. 6, 2021, pp. 14.
Chinese Office Action received in Chinese Application No. 201780028486.1 dated Nov. 8, 2021, pp. 12.
USPTO, Non-Final Rejection of the U.S. Exam Report on U.S. Appl. No. 16/300,323 (dated Feb. 8, 2023), 19 pages.
Zhang et al., "Nonionic Surfactant Application Patent Technology," China Light Industry Press, Mar. 31, 2001, pp. 1-2.
Chinese National Intellectual Property Administration, Chinese Second Office Action for App. No. 201780028415.1 (dated Sep. 5, 2022), pp. 1-17.
Second Chinese Office Action received in Chinese Application No. 201880031248.0 dated Feb. 17, 2023, pp. 4.
COSDNA, "Copperstone Kids Clear Sunscreen Lotion (SPF 50)", Nov. 24, 2016, pp. 1.

\* cited by examiner

Results for Evaluation of Whipped Gel Products Prepared with Various Propellants

| Propellant in Whipped Gel Products | Whippability | Stability of Resultant Whipped-foam |
|---|---|---|
| Nitrous Oxide |  Yes, |  Good, T= 12min |
| Carbon Dioxide |  Yes, |  Poor, T= 1min |
| Isobutane |  Yes, | Poor |
| Isopentane |  Yes, |  Fair, T= 5min |
| Isobutane / Isopentane |  Yes, |  Fair, T= 1min |

FIGURE 1

Results for Evaluation of "Whipped-foam" Delivered from Whipped Aqueous Aloe Gel

| Whippability | Stability of Resultant Whipped-foam |
|---|---|
| Yes,  |  Fair        T=5min |

FIGURE 2

WHIPPED GEL FORMULATIONS

TECHNICAL FIELD

This invention relates to the field of whipped or whippable gel formulations. More specifically, the invention relates to whipped or whippable gel formulations, such as for topical application, such as, for example, sunscreen gel.

BACKGROUND

A key factor for ensuring the effectiveness of a formulation, such as sunscreen, skincare, vitamins for oral administration, woundcare for animals or humans, whip cream, haircare, medical hair and scalp treatments, topical analgesics, skin protection, etc. is end-user compliance and satisfaction.

For example, sunscreen labeling requirements instruct the consumer to "apply liberally", and to "reapply every 80 minutes and after swimming, sweating or toweling dry." Yet, reporting through the Academy of Dermatology website, dermatologists have noted that consumers typically do not apply enough sunscreen. This observed behavior, at least in part, may be because currently available sunscreens are sometimes perceived as heavy, sticky or greasy and can be aesthetically unpleasing during the application process. Also, current sunscreen lotion products have a tendency to become runny or drippy after application. Spray Aerosol sunscreen applications, which atomize low viscosity suncreen product, can be perceived as not providing even coverage, wasteful from overspray, or difficult to apply in windy situations; they can also be drying to the skin. Ideally, the sunscreen formulation should be easily applied to the skin of the user, and have a good texture and "feel" on the skin of the users.

Likewise, other products, such as for skincare, vitamins for oral administration, woundcare for animals or humans, whip cream, for haircare, for medical hair and scalp treatments, for topical analgesics, for skin protection, etc. could benefit from being administered as a whipped product, without the possibility of abuse.

SUMMARY

This disclosure provides a formulation in a package, which may be pressurized. The formulation is a gel. The formulation comprises one or more active agents that is co-mingled (co-processed) with a whipping agent (e.g., a gas propellant; a first gas propellant) prior to being filled under pressure into the package. The whipping agent is added in sufficient amounts to be dispersed in the formulation. In certain embodiments, the package maintains at least a minimal amount of pressure until substantially all the formulation in the package is expelled as a whipped formulation. In certain embodiments, the package maintains at least a minimal amount of pressure to maintain the whipping agent dispersed in the formulation. In certain embodiments, the pressurized package comprises a pressure generating and maintaining component. In certain embodiments, the component comprises one or more (second) gas and/or liquid propellants. In certain embodiments, the component is present in the package in sufficient amounts and pressure to expel the formulation as a whipped formulation upon application of external force on the formulation in the package. In certain embodiments, the amounts of the pressure generating and maintaining component are sufficient to expel substantially all the formulation in the package as a whipped formulation. In certain embodiments, the one or more second gas and/or liquid propellants do not co-mingle with the formulation.

In other aspects, this disclosure provides a method of preparing a whippable formulation, comprising: Filling a formulation comprising one or more active agents co-mingled (co-processed) with a whipping agent under pressure into a package, which may be pressurized; wherein the gas propellant is added in sufficient amounts to be dispersed in the formulation. The formulation is a gel. In certain embodiments, the package is under sufficient pressure suitable to maintain the whipping agent dispersed in the formulation. In certain embodiments, the package is under sufficient pressure to expel the formulation as a whipped formulation upon application of external force on the formulation in the package. In certain embodiments, the method is performed under controlled temperature. In certain embodiments, the package maintains at least a minimal amount of pressure until substantially all the formulation in the package is expelled as a whipped formulation. In certain embodiments, the package comprises a pressure generating and maintaining component. In certain embodiments, the component comprises one or more (second) gas and/or liquid propellants; the pressure generating and maintaining component is present in the package in sufficient amounts and pressure to expel the formulation as a whipped formulation upon application of external force on the formulation in the package; and wherein the one or more gas and/or liquid propellants do not co-mingle with the formulation.

In other aspects, this disclosure provides a method of using a formulation that is a whipped gel formulation product disclosed herein, comprising administering the formulation to a subject (user) in need thereof.

In other aspects, this disclosure provides a package comprising the formulation disclosed herein.

Numerous other aspects are provided in accordance with these and other aspects of the invention. Other features and aspects of the present invention will become more fully apparent from the following detailed description and the appended claims.

DETAILED DESCRIPTION

As used herein, the word "a" or "plurality" before a noun represents one or more of the particular noun. For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about," whether or not the term is explicitly used, unless explicitly stated otherwise. As used herein, the singular forms "a," "an," and "the" include plural referents unless the context clearly dictates otherwise.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

This disclosure provides a formulation in a package, which may be pressurized. The formulation comprises one or more active agents that is co-mingled (co-processed) with a whipping agent (e.g., a gas propellant; a first gas propellant) prior to being filled under pressure (and in certain embodiments under controlled temperature) into the package. The formulation is a gel. The whipping agent is added in sufficient amounts to be dispersed in the formulation. In certain embodiments, the package maintains at least a minimal amount of pressure until substantially all the formulation in the package is expelled as a whipped formulation. In certain embodiments, the package maintains at least a minimal amount of pressure to maintain the first gas dispersed in the formulation. In certain embodiments, the package comprises a pressure generating and maintaining component. In certain embodiments, the component comprises one or more (second) gas and/or liquid propellants. In certain embodiments, the component is present in the package in sufficient amounts and pressure to expel the formulation as a whipped formulation upon application of external force on the formulation in the package. In certain embodiments, the amounts of the pressure generating and maintaining component are sufficient to expel substantially all the formulation in the package as a whipped formulation. In certain embodiments, the one or more gas and/or liquid propellants do not co-mingle with the formulation.

No UV filter substances are used for the foam-boosting of self-foaming.

In certain embodiments, the formulation is expelled from the package without shaking the package.

The disclosed whipped formulation may be referred to herein as whipped formulation, whipped formulation product, whipped product, whipped gel, and the like.

The disclosed whippable formulation may be referred to herein as whippable formulation, whippable formulation product, whippable product, whippable gel, and the like.

A whipped formulation is at one time a whippable formulation.

The term "can" may be used to also mean "package."

A subject may be a human subject (user) or may be an animal subject (user). The terms "subject" and "user" are used interchangeably.

In other aspects, this disclosure provides a method of preparing a whippable formulation, comprising: Filling a formulation comprising one or more active agents co-mingled (co-processed) with a whipping agent (e.g., a gas propellant; a first gas propellant) under pressure into a package; the whipping agent is added in sufficient amounts to be dispersed in the formulation. The formulation is a gel. In certain embodiments, the package is under sufficient pressure suitable to maintain the whipping agent dispersed in the formulation. In certain embodiments, the pressurized package is under sufficient pressure to expel the formulation as a whipped formulation upon application of external force on the formulation in the package. In certain embodiment, the method is performed under controlled temperature. In certain embodiments, the package maintains at least a minimal amount of pressure until substantially all the formulation in the package is expelled as a whipped formulation. In certain embodiments, the package comprises a pressure generating and maintaining component; in certain embodiments, the component comprises one or more (second) gas and/or liquid propellants; the pressure generating and maintaining component is present in the package in sufficient amounts and pressure to expel the formulation as a whipped formulation upon application of external force on the formulation in the package; and wherein the one or more gas and/or liquid propellants do not co-mingle with the formulation.

In other aspects, this disclosure provides a method of using a formulation that is a whipped gel formulation product disclosed herein, comprising administering the formulation to a subject (a user) in need thereof. The user may be a human user.

In other aspects, this disclosure provides a package comprising a whippable gel formulation; the package may be pressurized. The formulation comprises one or more active agents and is co-mingled (co-processed) with a whipping agent (e.g., a gas propellant; a first gas propellant) prior to being filled under pressure (and in certain embodiments under controlled temperature) into the package. In certain embodiments, the package maintains at least a minimal amount of pressure until substantially all the formulation in the package is expelled as a whipped formulation. In certain embodiments, the package maintains at least a minimal amount of pressure to maintain the whipping agent dispersed in the formulation. In certain embodiments, the package comprises a pressure generating and maintaining component. In certain embodiments, the component is present in the package in sufficient amounts and pressure to expel the formulation as a whipped formulation upon application of external force on the formulation in the package. In certain embodiments, the amounts of the pressure generating and maintaining component are sufficient to expel substantially all the formulation in the package as a whipped formulation. In certain embodiments, the pressure generating and maintaining component comprises one or more (second) gas and/or liquid propellants which are not co-mingled with the formulation. In certain embodiments, the one or more gas and/or liquid propellants do not co-mingle with the formulation.

In certain embodiments, the disclosed formulations and methods allow for very high levels of inert gas dissolved into the product and effectively held under pressure in a gas-emulsion, preventing unwanted bubble agglomeration, providing for highly uniform product characteristics. The result is a "whipped" gel that provides confidence of sunscreen coverage (in the case where the product is a sunscreen), while offering surprisingly fast "rub-in"; while not altering the inherent moisturization and protection properties of the otherwise base formulation.

Whippable products include, in addition to for skincare and suncare (Sunscreen and After Sun care), for example and without limitation:

Category—Class—Whipped Benefit
Whip Cream—Food—Anti-Abuse
Peanut Butter—Food—Ease of Application
Dessert Topping—Food—Ease of Application
Topical Analgesic—OTC Drug—Improved Absorption
Burn Cream—Medical Device Rx—Reduced Spreadability Pain
Medical Haircare—Hair loss—NDA—Reduced Consumer Complaints—Failure to empty
Medical Haircare—Scalp treatment—OTC Drug-Improved Delivery/Application
Petrolatum Gel—OTC Drug—Ease of Application Hair Styling Product—Cosmetic—Novel Delivery of Thicker Products Diaper Rash Prevention—OTC Drug—Novel Delivery of Thicker Products Tooth Whitener—Cosmetic—Better Coverage Oral Care—Toothpaste—Cosmetic—Improved Delivery Anti-Fungal treatment—OTC/Rx Drug—Reduced Spreadability Pain/Improved Absorption Eye-lid Cleanser—Cosmetic—Novel Delivery Psoriasis treatment—Medical Device—Reduced Spreadability Pain Colon-Rectal Treatment—Rx—Improved Drug Delivery and Absorption Acne treatment—OTC Drug—Novel Delivery Hand Sanitizer—OTC Drug—Formulation Approach Natural Deodorant—Cosmetic—Improved Spreadability Shave Prep—Cosmetic—Novel Delivery of Thicker Products Wound Care—Medical Device—Novel Delivery of Thicker Products Self-Tanner—Cosmetic—Improved Delivery Body Moisturizer—Cosmetic—Novel Delivery of Thicker Products Lice Treatment—Medical Device/OTC—Novel Delivery of Thicker Products Hair Depilatory—OTC Drug—Novel Delivery of Thicker Products Anti-Hemorrhagic—Rx/Device—Formulation Compatibility—Non-Flammability—Surgical Application.

Thus, in certain embodiments, to the extent that the products listed above are gel formulations, the formulations disclosed herein comprise one or more active agents for each of the above formulations.

In certain embodiments, the whipped gel formulation product is a skincare product, comprising one or more skincare active agents. In certain embodiments, the whipped formulation product is a sunscreen or an After-Sun product. In certain embodiments, the whipped formulation product may be an oral dosage form, such as a whipped multi-vitamin product. In certain embodiments, the whipped formulation product may be for woundcare of animals or humans. The whipped formulation may also be, for example, whip cream, for haircare, for medical hair & scalp treatments, topical analgesics, or for skin protection.

In certain embodiments, the formulation further comprises a foaming agent. In certain embodiments, the formulation is for topical application.

In certain embodiments, the pressurized package in which pressure may be generated and/or maintained sufficient for the disclosed formulations is a Bag-on-valve, Piston Can, or Bag-in-Can. In other embodiments, the pressurized package is a mechanical pressure system, including for example, bladder system (such as Exxal Atomos System), which is a PowerContainer system with a rubber bladder around the outside providing pressure to the internal volume. In certain embodiments, springs are used to exert pressure on a bag. In certain other embodiments, hydrostatic pressure is used to exert pressure on a bag.

In certain embodiments, the package is a bag on valve (BOV) pressurized assembly, comprising a two-way fill/dispensing valve, an attached internal high barrier bag affixed to the valve, and rigid container adapted to and capable of holding positive pressure, affixed to the valve. In certain further embodiments, the container is glass, barrier resin, metal/alloy, or another material capable of holding positive pressure. In certain other further embodiments, the container is pre-pressurized with one or more gas and/or liquid propellants prior to filling. In certain further embodiments, the BOV pressurized assembly dispenses the whipped product in a metered dispensing system and not a continuously dosing system.

In certain embodiments, the pressurized package can comprise a "pressure generating and maintaining component," which may be a component that generates and/or maintains pressure in the package. It may refer to a chemical component or components which generate pressure, e.g., compressed gas, while inside an enclosed package, device or container (such as a can, for example). Non-limiting examples of such pressure generating and maintaining components are compressed gases/propellants and liquid propellants such as, for example, $CO_2$, propane, butane, isobutane, dimethyl ether, nitrous oxide, nitrogen, oxygen, air, isopentane, hydrofluroolefin, and the like, and suitable blends of such propellants. When a valve is opened by applying an external force, the formulation or ingredients in the device are dispensed in a 'whipped' form or a foamy form. This chemical component or components does not co-mingle with the formulation and may not be dispended with the whipped formulation.

In certain embodiments, pre-pressurizing the package is not needed. In certain embodiments, the package is under Zero Cut Bag Pressure, where gas is present around bag but not pressurized above ambient. Filling the package at ambient pressure, the pressure inside the package would increase as the BOV expands. In certain embodiments, the package comprises an elastomeric tube/bag (akin to a tied off surgical tube). In certain further embodiments, a slight vacuum is applied. In certain embodiments, the package is pressure agnostic, in which the container cannot hold pressure around the bag. In certain embodiments, the package has Negative Cut Bag Pressure, where vacuum is present around the bag but not pressurized above ambient. Other such systems may be used, such as the Sterilflo® system (https://www.hydrasense.ca/en/why-choose-hydrasense/steriflo/).

In certain embodiments, the gel formulation is an alcohol gel formulation. In certain embodiments, the gel formulation comprises between 25% to 60% alcohol.

A "skincare active agent" includes all those materials which are regarded as acceptable for use as active skin-protecting ingredients. A skincare active agent includes, for example and without limitation, skin protectant and/or anti-aging agent. Approval by a regulatory agency may sometimes be required for inclusion of active agents in formulations intended for human contact including but not limited to sunscreen active ingredients or petrolatum, white petrolatum, mineral oil, and dimethicone as skin protectants, as well as agents used as self-tanners or for diaper rash treatment and the like.

Sunscreen active agents that have been or are currently approved for sunscreen use in the United States and elsewhere include, without limitation, paraaminobenzoic acid, avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, octisalate, sulisobenzone, trolamine salicylate, titanium dioxide and zinc oxide, diethanolamine methoxycinnamate, digalloyl trioleate, ethyl dihydroxypropyl PABA, glyceryl aminobenzoate, lawsone with dihydroxy acetone, red petrolatum and the like. Several other sunscreen active ingredients are accepted for use in other countries. Some non-limiting examples from outside the U.S. include Tinosorb M, Tinosorb S, Uvinul T-150, UVA sorb HEB, Uvinul A Plus, Neo Heliopan AP, Neo Heliopan MBC, and the like. It is typical to use combinations of two or more skincare active agents in a formulation. Preferably, the amount of skincare active agent or agents is present in an amount that is consistent with the FDA guidelines. In other embodiments, the amount of skincare active agent or agents is present in an amount that is consistent with other regulatory bodies. The use of a combination of active agents is especially true for sunscreen formulations to achieve higher levels of ultraviolet absorption or to provide useful absorption over a wider range of ultraviolet wavelengths than can be the case with a single active component. The sunscreen active agent or agents may be present in an amount that is consistent with the FDA sunscreen monograph for sunscreen active agent or agents that are believed to provide the requisite SPF in accordance with the FDA monograph for such sunscreens. Other skin care active agents include sunless tanning active agents, skin protectant active agent emollients, insect repelling agents, and the like. And other agents known in the art.

After Sun product is specially formulated to cool, soothe, calm, and re-hydrate (moisturize) a sunburnt or stressed skin, and to lessen the pain or itch of a sunburnt body. Currently, After Sun products are available as lotion, cream, gel, or spray. The active agents in them are known in the art and any of which is within the scope of this invention. After Sun Actives are ingredients that can provide the following (but not limited) effects on skin: cooling; soothing; calming; re-hydrating (moisturizing); or relief pain/itch associated with sunburn. As an example, and without limitation, an After Sun formulation contains Glycerin, Panthenol, and Aloe Barbadensis Leaf Juice to provide cool and moisturizing effects on skin. As another example, and without limitation, another After Sun formulation contains Lidocaine as an active to provide sunburn pain/itch relief.

Other active agents are contemplated. These include, for example and without limitation, sunscreen active agents, After Sun active agents, vitamins, food, etc. Any active agents that can be included as a whipped gel formulation or a whippable gel formulation are within the scope of this invention.

In certain embodiments, the package does not display any bearding. Bearding is leakage forced by continued expansion of product still contained within the flow channel of the actuator.

In certain embodiments, the package does not need to be shaken to dispense the formulation.

In certain embodiments, the formulation is characterized by microdispersion. In certain embodiments, the formulation is characterized by substantially consistent microvoid after the formulation is expelled from the package. In certain embodiments, the formulation is highly emollient after the formulation is expelled from the package. In certain embodiments, the formulation is readily spreadable and spread evenly after the formulation is expelled from the package.

In certain embodiments, the whipping agent (co-mingled or co-processed with the formulation comprising one or more active agent) is nitrogen, nitrous oxide, carbon dioxide, Argon, air or oxygen. In certain embodiments, the gas propellant in the formulation is between about 0.01% w/w to about 15.00% w/w.

In certain embodiments, the formulation has one or more of characteristics such as little or no wetness after application, having a collapse time of at least 60 seconds, or structurally stable for at least 30 minutes.

In certain embodiments, the formulation is a sunscreen and the one or more active agents include one or more sunscreen active agents.

The disclosed whipped formulation product represents the careful culmination of advancements in formulation, processing, and packaging to meet the end result of delivering a rich, creamy, spreadable, lightweight whipped product for consumer application.

Formulation:

Non-shear thickening emulsion chemistries have been developed to allow for high levels of gas dispersion, physical stability during temperature and pressure extremes, and post-dispensing foam stability. The chemistries have also been customized to allow for the inclusion of consumer-relevant ingredients that may include, for example and without limitation, sun screens, moisturizers, emulsifying agents, film forming agents, thickening agents, skin feel aesthetic enhancers, antifungals, pH adjusters, pro vitamin additives, physical skin barriers, anti-bacterial agents, skin colorants, etc. Other ingredients are also contemplated, such as, without limitation, pain relief additives.

Processing:

In processing of some embodiments, the blended formulation is transferred into a hopper, pressurized and under a controlled temperature, rate of flow and pressure, and is transferred into a high shear, continuous-flow, high-pressure "whipping" head, which rapidly mixes the base formulation with a series of infusion gas injector ports which controls the gas pressure and rates of flow with a selection of gases (or gas) to rapidly co-mingle the gas and formulation solution, effectively "saturating" the gas into the formulation prior to injection into the package. The gas-infused formulation is then tested for density inline and controlled under pressure and finally injected under pressure into the desired package.

In certain embodiments, the whipping agent is a suitable gas. In certain embodiments, the whipping agent is co-mingled with the formulation prior to filling the formulation into the package.

In certain embodiments, the whipping agent is co-mingled with the formulation prior to filling the formulation/gas into the package.

In certain embodiments, the gas is nitrous oxide gas. In certain embodiments, the nitrous oxide in the formulation is about 0.1% w/w to about 4.0% w/w. In certain embodiments, the nitrous oxide in the formulation is about 0.1% w/w to about 10.0% w/w. In certain embodiments, the Nitrous Oxide in the formulation is about 0.1% w/w to about 1.9% w/w. In certain embodiments, the nitrous oxide in the formulation is about 0.1%, 1.0%, 1.9%, 2.0%, 3.0%, 4.0%, 5.0% w/w to about 6%, 7%, 8%, 9%, 10 w/w. Nitrous oxide has a slight sweet odor that can contribute to fragrance benefits (dual purpose gas benefits).

In certain embodiments, certain other gases can serve as a particularly good whipping agent, as evaluated by the known or estimated Ostwald Coefficients of the blended mixture and gases. Taking into consideration the potential negative effects of co-mingling of the gases with base blended formulation, example being $CO_2$, which can react with water-containing formulas to create carbonic acid and cause shifts in product pH. Alternatively, $CO_2$ can be used as a whipping gas to deliberately modify the pH of the formulation to reach targeted pH levels. Gas propellant or combinations include, without limitation, $CO_2$, argon, isobutane, nitrogen, Argon, air, oxygen, isopentane, other suitable gases, and combination thereof.

In certain embodiments, the gas propellant in the formulation is between about 0.01% w/w to about 15.00% w/w.

In certain embodiments, the whipping agent is an aerosol propellant (including hydrocarbon propellant, compressed gas propellant, soluble gas propellant, and liquefied gas propellant) or a liquid propellant.

In certain embodiments, the whipping agent is a gas propellant. The gas propellant is, for example and without limitation, nitrogen, nitrous oxide, carbon dioxide, Argon, air or oxygen. In certain embodiments, the gas propellant in the formulation is between about 0.01% w/w to about 15.00% w/w.

In certain embodiments, the whipping agent is a liquefied gas propellant, which includes, for example and without limitation, propane, isobutene, N-butane, Dymel 152a, 134a, hydrocarbons, DME (dimethyl ether), 1,3,3,3-tetrafluoropropene, and HFCs (1,1,1,2-tetrafluoroethane).

In certain embodiments, the whipping agent is a hydrocarbon propellant, which includes, for example and without limitation, methane, ethane, propane, butanes, and pentanes.

Unless otherwise noted or otherwise clear in context to a person of ordinary skill in the art, all % herein are weight to weight (w/w).

Packaging:

In certain embodiments, the pressure in the pressurized package is initially between about 15 psig to about 60 psig. In certain embodiments, the final pressure in the pressurized package is between about 80 psig to about 160 psig. In certain embodiments, the pressure initially is about 40 psig to 45 psig. In certain embodiments, the final pressure is about 110 psig to 120 psig.

In certain embodiments, the package is a Bag on Valve (BOV) pressurized assembly, comprising a two way fill/dispensing valve, an attached internal high barrier bag (affixed to valve), and rigid container capable of holding positive pressure (affixed to the valve). The container may be glass, barrier resin, metal/alloy, or another material capable of holding positive pressure. The container may be "pre-pressurized" with a combination of gaseous and/or liquid propellants prior to filling, with internal pressure expected to build as the internal volume is displaced during pressurized BOV filling.

The Bag on Valve assembly and accompanying "air gap" created between bag and the pressurized rigid container help to create an insulated barrier between the formulation and the user environment. This isolative barrier is helpful to moderate the temperature swings that might be experienced when taking this product from an ambient (indoor) location to a cooler or warmer environment, such as into the sun or into vehicles located in low/high temperature environments. This barrier helps to buffer formulation temperature change and help the formulation deliver a more consistent product experience (lower temperatures can form more rigid foam structures and high temperatures can cause weaker foam structures). This feature can be particularly useful for products formulated with lower melt point foam-formers, intended for use in elevated temperature environments.

Bag on Valve delivery systems differ from traditional aerosol delivery systems in at least the following district ways: Aerosols require propellant gases to be co-joined or co-mingled into the base formulation, as would be the case in single or multiphase system. These systems use the propellant gas to both expel the product and as a foaming and/or particle breakup agent. By contrast, a Bag on Valve system includes the use of a bag within a metal can. The bag is in direct contact with the single phase formulation and is expelled by application of pressure to the outside of the bag. As such, the propellant gas inside the package never comes in contact with the product. Particle breakup or foaming can be accomplished through the dispensing actuator design and/or through the inclusion of a secondary gas within the formulation.

This BOV design has a several distinct benefits over traditional aerosol systems including without limitation:

Very high levels of product evacuation (>99% or even greater than 99.5%)

The ability to dispense formulas without the need to comingle with the propellant gas ("pure" formulation concentrate)

The ability to use two different gases within the system, one optimized as a propellant and one optimized as a foaming, forming (put in hand etc) or particle breakup additive.

The ability to use two different gases within the system, one optimized as a propellant and one optimized as a foaming, forming (i.e., dispensing the formulation on a user's hand in a specific, desired form) or particle breakup additive.

For example, in certain embodiments, nitrous oxide is used as a whipping agent without allowing "free gas" to be expelled and potentially abused. By contrast, whipped cream packaging which is sold in a traditional aerosol permits the user the ability to release and potentially abuse the gas propellant/whipping agent.

The pressure generating and maintaining component may be a gas, such as gaseous propellant, a liquid, such as a liquid propellant or a blend of gas and liquid. As used herein, a gaseous propellant may also be a compressed gas, such as $CO_2$, nitrous oxide and the like. As used herein, a liquid propellant may also be a liquefied gas, such as isobutane and the like.

The pressure generating and maintaining component can be formulated inside the device in a variety of ways, depending upon the nature of the component or components that form the pressure generating and maintaining component. The vehicle, while acting as pressure-generator, may be a gas, even though it may have been packaged as, for example, a gas, a liquid or a solid. Non-limiting examples of the gas are carbon dioxide ($CO_2$), nitrous oxide ($N_2O$) and the like. Thus, for example, if the vehicle is carbon dioxide, the carbon dioxide can be 'derived' inside the sealed pressurized container in several ways. For example, the gas could be pumped into the container, or it could be added into the ingredients as "dry ice", or it could be derived or generated in situ via the chemical reaction of a suitable base with a suitable acid. In the case of "pumped in" or "dry ice", the gas is already present as $CO_2$. In the case of generation in situ via the chemical reaction of a base with an acid, the gas is generated when the acid and the base mix.

If generating the gas by chemical reaction between a base and an acid, non-limiting examples of suitable bases include sodium bicarbonate, sodium carbonate, potassium bicarbonate, potassium carbonate and the like. Non-limiting examples of suitable acids include acetic acid, citric acid and the like. Sodium bicarbonate with citric acid is a suitable combination. Because the components are being combined inside of the sealed container (device), the gas produced during the reaction is trapped which pressurizes the container.

One advantage of the inventive system is that the gas introduced or produced may be non-flammable.

In certain embodiments, the whipped formulation product is characterized by microdispersion. In certain embodiments, the whipped formulation product is characterized by substantially consistent microvoid.

In certain embodiments, the whipped formulation product comprises at least one recognized skincare active agent.

In certain embodiments, the whipped gel formulation is a sunscreen formulation comprising at least one sunscreen active agent.

In certain embodiments, the whipped gel formulation product further comprises other ingredients, such as, for example and without limitation, one or more fatty alcohols—selected from, for example and without limitation, cetyl alcohol, stearyl alcohol, myristyl alcohol, hydroxystearyl alcohol, oleyl alcohol, isostearyl alcohol, lauryl alcohol, hexadecyl alcohol, ricinoleyl alcohol, behenyl alcohol (lanette 22), erucyl alcohol and 2-octyl-dodecanol. In certain embodiments, the whipped formulation is an aftersun lotion (contains Cetyl alcohol) but may optionally be without any added behenyl alcohol.

In certain embodiments, the physical stability of the whipped products obtained may also be characterized by means of these tests: determination of the organoleptic characteristics (e.g., aspect, color, odor), characterization of the texture (e.g., thick, fluid, greasy, non-greasy), and characterization of the spreadability.

In one embodiment, the disclosed whipped product formulation dispenses in a continuous stream when an external pressure is applied to the device, such as by depressing the valve/actuator, thereby eliminating the need to squeeze and shake the formulation out of a bottle or tube.

In another embodiment, the disclosed whipped product in its device (package) operates as a "one-touch" delivery system; in such system, the user will hold down the actuator until the desired amount of formulation is dispensed.

In another embodiment, the disclosed whipped product in its package offers a continuous delivery system for an application, such as, for example and without limitation, skincare applications and suncare applications. Traditionally, "continuous delivery" is typically offered as a spray product and has been very successful due to the ease and speed that it provides for sunscreen application. Many consumers, however, prefer lotions/gels over sprays and would benefit from a continuous delivery mechanism. The present invention offers such an advantage.

In certain embodiments, the gel formulation is anhydrous and is an alcohol gel formulation (thus comprises alcohol). The gel formulation comprises one or more film forming agents, one of which is TM-Si 5. The gel formulation comprises active agent(s), which differs based on the purpose of the gel formulation. For example, a gel sunscreen formulation would comprise sunscreen active agents. In certain embodiments, the gel formulation comprises one or more emollients. In certain embodiments, the formulation comprises one or more viscosity increasing agents. In certain embodiments, the one or more viscosity increasing agents include fumed silica, for example, surface-treated fumed silica. In certain embodiments, a surface-treated fume silica is a surface-treated fume silica with polydimethylsiloxane (such as Aerosil® R202). A formulation comprising fumed silica has superior sensory characteristics (e.g., better skin feel, appearance, etc.) than one without. The formulation optionally comprises other ingredients. Such optional ingredients include: a skin conditioning and/or bulking agent, for example, a silicone elastomer, which may give a powdery feel to the product after the alcohol has evaporated rather than an oily feel; a fragrance, such as, for example and without limitation, Fragrance SZ-2108 MOD 2010 (INCI name: fragrance); etc.

In certain embodiments, the gel formulation comprises the emollient Dragoxat 89 (INCI name: Ethylhexyl Isononanoate), which provides the final product a dry feel. Its ester is made from the reaction of isononanoic acid and 2-ethylhexanol and is a low viscous dry emollient, it is a colorless clear liquid, neutral odor with high purity. In certain embodiments, the gel formulation comprises about 1% to about 10% of Dragoxat 89 (INCI name: Ethylhexyl Isononanoate); in further embodiments, the gel formulation comprises about 5% of Dragoxat 89 (INCI name: Ethylhexyl Isononanoate).

In certain embodiments, the gel formulation comprises the emollient Dicaprylyl Ether (INCI name: Dicaprylyl Ether). Dicaprylyl Ether is an ether of coconut oil (or other plant based oil) derived caprylic acid. In certain embodiments, the gel formulation comprises about 1% to about 10% of Dicaprylyl Ether; in further embodiments, the gel formulation comprises about 5% of Dicaprylyl Ether.

An example of a silicone elastomer is Dow Corning 9701 Cosmetic Powder (INCI Name: Dimethicone/Vinyl Dimethicone Crosspolymer). It is a copolymer of dimethylpolysiloxane crosslinked with vinyl dimethylpolysiloxane. It may provide the final product with a silky, powdery feel. In certain embodiments, the gel formulation comprises about 1% to about 5% Dimethicone/Vinyl Dimethicone Crosspolymer; in certain further embodiments, the gel formulation comprises about 2% Dimethicone/Vinyl Dimethicone Crosspolymer.

In certain embodiments, the gel formulation comprises 25% to about 90% alcohol; in further embodiments, the gel formulation comprises between about 40% to about 55% alcohol. Any suitable alcohol may be used. In certain embodiments, an alcohol that is suitable for skincare is used. In certain embodiments, the alcohol comprises a short-chain alcohol. In certain embodiments, the alcohol is ethanol, methanol, isopropanol, and blends thereof. In certain embodiments, the alcohol is denatured. In some embodiments, the alcohol is denatured ethanol (SD alcohol 40-B).

TM-Si 5 (chemical name: octyldodecyl/glyceryl hydroxy stearate dilinoleate dimethicone copolymer, INCI Name: Polyester-27, by SurfaTech Corporation, Lawrenceville GA USA) is a film forming polymer; it is a water proofing/water resistant agent. In certain embodiments, the formulation comprises about 1% to about 5% TM-Si 5. In certain embodiments, the formulation comprises about 3% TM-Si 5.

In certain embodiments, the formulation comprises additional film forming agent(s). In certain embodiments, an additional film forming agent is Allianz™ OPT.

Allianz™ OPT (INCI Name: Acrylates/C12-22 Alkylmethacrylate Copolymer; Ashland) is the tetrapolymer emulsion polymerization product of methacrylic acid, methyl methacrylate, butyl acrylate and cetyl-eicosinyl methacrylate. It is a very hydrophobic, high molecular weight, crosslinked polymer. It effectively thickens the oil phase by creating a large hydrophobic network. In certain embodiments, the gel formulation comprises about 0.1% to about 1% Allianz™ OPT. In certain embodiments, the formulation comprises about 0.5% Allianz™ OPT.

In certain embodiments, the film forming agent (gellant) is a thickening agent for thickening alcohol-based solutions.

In certain embodiments, a film forming agent is FlexiThix™ polymer. FlexiThix™ polymer (INCI name: polyvinylpyrrolidone; Ashland, Columbus OH USA) is a thickener/gellant that works under extreme conditions. Capable of providing stability across a wide pH range, this polymer is highly tolerant of salt, provides a pleasant after-feel and requires no neutralization. In certain embodiments, the formulation comprises about 1% to about 5% FlexiThix™ polymer. In certain embodiments, the formulation comprises about 3% FlexiThix™ polymer.

In certain embodiments, the gel formulation comprises the film forming agent Wax White NF Pellets (INCI name: Beeswax). In certain embodiments, the gel formulation comprises about 0.1% to about 1% Beeswax; in certain further embodiments, the gel formulation comprises about 0.5% Beeswax.

In certain embodiments, the formulation comprises about 0.1% to about 1% fumed silica, such as fumed silica surface-treated with polydimethylsiloxane (such as Aerosil® R202). In certain embodiments, the formulation comprises about 0.7% fumed silica, such as surface-treated with polydimethylsiloxane (such as Aerosil® R202).

Aerosil® R202 (INCI name: Silica Dimethicone Silylate) is a fumed silica surface-treated with polydimethylsiloxane (a viscosity increasing agent). Its chemical name is silicones and siloxanes, dimethyl, reaction products with silica. It may provide the final product a no shine, matt finish.

In certain embodiments, the gel formulation comprises: alcohol; one or more film forming agents, one of which is octyldodecyl/glyceryl hydroxy stearate dilinoleate dimethicone copolymer; active agent(s), such as sunscreen active agents to make a sunscreen gel formulation; a viscosity increasing agent, such as a fumed silica; additional film forming agents, such as Acrylates/C12-22 Alkylmethacrylate Copolymer, Beeswax, and/or polyvinylpyrrolidone, and a skin conditional agent, such as a silicone elastomer, such as Dimethicone/Vinyl Dimethicone Crosspolymer; emollient(s), such as Ethylhexyl Isononanoate and Dicaprylyl Ether; (optionally) fragrance and/or other optional ingredients. The percentages of these ingredients may be those listed herein.

As stated, in certain embodiments, the gel formulation comprises one or more emollients. An emollient helps to smooth and soften the skin, and may also reduce its roughness, cracking or irritation. Non-limiting examples of suitable emollients include, for example and without limitation, mineral oil having a viscosity in the range of 50 to 500 centipoise (cps), lanolin oil, coconut oil, cocoa butter, olive oil, almond oil, macadamia nut oil, aloe extracts such as aloe vera lipoquinone, synthetic jojoba oils, natural Sonora jojoba oils, safflower oil, corn oil, liquid lanolin, cottonseed oil and peanut oil. In certain embodiments, the emollient is a cocoglyceride, which is a mixture of mono, di and triglycerides of cocoa oil, or Dicaprylyl Ether. Another suitable emollient is, for example, DC 200 Fluid 350, a silicone fluid.

Other suitable emollients may include, for example and without limitation, squalane, castor oil, polybutene, sweet almond oil, avocado oil, calophyllum oil, ricin oil, vitamin D, vitamin E acetate, olive oil, silicone oils such as dimethylopolysiloxane and cyclomethicone, linotenic alcohol, oleyl alcohol, the oil of cereal germs such as the oil of wheat germ, isopropyl palmitate, octyl palmitate, isopropyl myristate, hexadecyl stearate, butyl stearate, decyl oleate, acetyl glycerides, the octanoates and benzoates of ($C_{12}$-$C_{15}$) alcohols, the octanoates and decanoates of alcohols and polyalcohols such as those of glycol and glyceryl, ricinoleates esters such as isopropyl adipate, hexyl laurate and octyl dodecanoate, dicaprylyl maleate, hydrogenated vegetable oil, phenyltrimethicone, jojoba oil and aloe vera extract.

Other suitable emollients that are solids or semi solids at ambient temperatures may be used. Such solid or semi-solid cosmetic emollients include, for example and without limitation, glyceryl dilaurate, hydrogenated lanolin, hydroxylated lanolin, acetylated lanolin, petrolatum, isopropyl lanolate, butyl myristate, cetyl myristate, myristyl myristate, myristyl lactate, cetyl alcohol, isostearyl alcohol and isocetyl lanolate. One or more of these emollients can be optionally included in the formulation.

In certain embodiments, the gel formulation is aqueous, such as a hair spray.

The disclosed whipped formulation product can be used for any application that would benefit from such product, including, for example and without limitation, skincare, sunscreen, After Sun care, vitamins, woundcare, etc. For each application, the formulation needs to comprise the corresponding active agent(s) and may further comprise other appropriate ingredients.

The disclosed whipped product dispenses in a light whipped form, infused with tiny bubbles that make the texture of the formulation lighter, smoother and easier to spread across the skin. This texture also makes the formulation feel less greasy and more aesthetically pleasing on hands and skin, leaving a 'sumptuous' feel with a sun-screen during application. This formulation spreads quickly and disappears rapidly as the user rubs the formulation into the skin. Such a formulation may even prevent excess application of the agent and may offer ecological advantages.

In another embodiment, the disclosed whipped product offers an easier, faster, smoother, and less greasy skincare formulation than a traditional formulation.

In certain embodiments, the whipped formulation product comprises one or more of a thickening agent.

It may be advantageous to incorporate thickening agents, such as, for instance, Avicel RC-591, Carbopol Ultrez, Carbopol ETD 2001, available from the B. F. Goodrich Co, Abil Wax 9801, a surfactant available from Evonik, Alginic Acid, available from Kelco, cellulose gum, available from TIC Gums, ammonium acrylates copolymer, ammonium polyacryloyl dimethyl taurate, bentonite available from Southern Clay, guar hydroxpropyltrimonium chloride available from Henkel, hydroxy propylprocellulose available from Aqualon, magnesium aluminum silicate, available from Salomon, potassium alginate available from Kelco, beeswax available from Strah & Pitsch, and behenyl alcohol available from Nikko.

Insect repelling components are also a desirable ingredient in certain skincare and sunscreen formulations, if the formulations are to be used by persons engaged in outdoor activities. The most widely used insect repelling agent for personal care products is N,N-Diethyl-m-toluamide, frequently called "DEET" and available in the form of a concentrate containing at least about 95 percent DEET. Other synthetic chemical repellents include, for example and without limitation, dimethyl phthalate, ethyl hexanediol, indalone, di-n-propylisocinchoronate, bicycloheptene, dicarboximide, IR3535 (3-[N-Butyl-N-acetyl]-aminopropionic acid, ethyl ester; available from Merck KGaA)) and tetrahydrofuraldehyde. Certain plant-derived materials also have insect repellent activity, including citronella oil and other sources of citronella (including lemon grass oil), limonene, rosemary oil and eucalyptus oil. Choice of an insect repellent for incorporation into the skincare or sunscreen emulsion will frequently be influenced by the odor of the repellent. The amount of repellent agent used will depend upon the choice of agent; DEET is useful at high concentrations, such as up to about 15 percent or more, while some of the plant-derived substances are typically used in much lower amounts, such as 0.1 percent or less.

The disclosed formulation/formulations may contain a wide range of additional, optional components. The CTFA Cosmetic Ingredient Handbook, Seventh Edition, 1997, the Eighth Edition, 2000, and the personal care council website (http://www.personalcarecouncil.org/) describe a wide variety of cosmetic and pharmaceutical ingredients commonly used in skin care formulations, which are suitable for use in the formulations of the present invention. Examples of these functional classes disclosed in these references include, for example and without limitation: absorbents, abrasives, anti-caking agents, anti-foaming agents, antioxidants, binders, biological additives, buffering agents, bulking agents, chelating agents, chemical additives, colorants, cosmetic astringents, cosmetic biocides, cryoprotectants, film stabilizers, denaturants, drug astringents, external analgesics, film formers, fragrance components, humectants, pacifying agents, pH adjusters, plasticizers, preservatives, propellants, reducing agents, skin bleaching agents, skin-conditioning agents (emollients, humectants, miscellaneous, and occlusive), skin protectants, solvents, SPF enhancers/boosters, foam boosters, hydrotropes, solubilizing agents, suspending agents (nonsurfactant), sunscreen agents, ultraviolet light absorbers, water-proofing agents, and viscosity increasing agents (aqueous and nonaqueous).

The whipped formulations can further comprise skin protectant active agents. Suitable examples include, for example and without limitation, (with preferred weight percent ranges), Allantoin (0.5 to 2 percent); Aluminum hydroxide gel (0.15 to 5 percent), Calamine (1 to 25 percent); Cocoa butter (greater than 50 percent); Cod liver oil (5 to 14 percent); Dimethicone (1 to 30 percent); Glycerin (20 to 45 percent); Hard fat (greater than 50 percent); Kaolin (4 to 20 percent); Lanolin (12.5 to 50 percent); Mineral oil (greater than 50 percent); Petrolatum (greater than 30 percent); Topical starch (10 to 98 percent); White petrolatum (greater than 30 percent); Zinc acetate (0.1 to 2 percent); Zinc carbonate (0.2 to 2 percent); and Zinc oxide (1 to 25 percent). Additional skin protectant active agents may include Colloidal oatmeal or Sodium bicarbonate.

An antimicrobial preservative may be part of the disclosed formulation. An antimicrobial preservative is a substance or preparation which destroys, prevents or inhibits the proliferation of, microorganisms in the skincare formulation, and which may also offer protection from oxidation. Typical preservatives include, for example and without limitation, the lower alkyl esters of para-hydroxyben-zoates (parabens), especially methylparaben, propylparaben, isobutylparaben and mixtures thereof, benzyl alcohol, phenyl ethyl alcohol and benzoic acid. The preferred preservative is available under the trade name of Germaben II from Sutton or a combination of chlorophenesin and benzyl alcohol. One or more antimicrobial preservatives can optionally be included in an amount ranging from about 0.001 to about 10 weight percent, preferably about 0.05 to about 1 percent.

An antioxidant may be part of the disclosed formulation. An antioxidant is a natural or synthetic substance added to the sunscreen to protect from or delay its deterioration due to the action of oxygen in the air (oxidation) and to protect the skin from sun damage. Antioxidants prevent oxidative deterioration which may lead to the generation of rancidity and nonenzymatic browning reaction products. Typical suitable antioxidants include, for example and without limitation, propyl, octyl and dodecyl esters of gallic acid, butylated hydroxyanisole (BHA, usually purchased as a mixture of ortho and meta isomers), butylated hydroxytoluene (BHT), nordihydroguaiaretic acid, Oxynex (Oxynex ST liquid is a mixture of diethylhexyl syringyliden-emalonate and caprylic/capric triglyceride), Vitamin A, Vitamin E and Vitamin C. One or more antioxidants can optionally be included in the formulation in an amount ranging from about 0.001 to about 5 weight percent, preferably about 0.01 to about 0.5 percent.

Chelating agents may be part of the disclosed formulation. Chelating agents are substances used to chelate or bind metallic ions, such as with a heterocyclic ring structure so that the ion is held by chemical bonds from each of the participating rings. Suitable chelating agents include, for example and without limitation, ethylene diaminetetraacetic acid (EDTA), EDTA disodium, calcium disodium edetate, EDTA trisodium, citric acid, EDTA tetrasodium and EDTA dipotassium. One or more chelating agents can optionally be included in the formulation in amounts ranging from about 0.001 to about 0.2 weight, percent preferably about 0.01% weight percent.

The disclosed formulation may include foam stabilizers or foam stabilizing agents. There are many examples of such agents and means to achieve foam stability. Non-limiting examples of suitable foam stabilizers include, for example and without limitation, the Avicels, Capmul S12L, Capmul S18L, Amilite GCK-12, Amadol CMA-2, Ampholak 7 CX-C, Ampholak X C0-30, Polyox WSR N-10, Amaranth S, Foam-Coll 5, Blanose 12M31XP, Genu carrageenan, Avanel S150CG and others. Avicel is an example that can be used in the formulation. For example, Avicel RC-591 is a mixture of cellulose gum and microcrystalline cellulose. Some foam stabilizers also help improve long term high temperature stability.

Fragrances are aromatic substances which can impart an aesthetically pleasing aroma to the skincare or sunscreen formulation and may be part of the disclosed formulation. Typical fragrances include, for example and without limitation, aromatic materials extracted from botanical sources (i.e., rose petals, gardenia blossoms, jasmine flowers, etc.) which can be used alone or in any combination to create essential oils. Alternatively, alcoholic extracts may be prepared for compounding fragrances. However, due to the relatively high costs of obtaining fragrances from natural substances, the modern trend is to use synthetically prepared fragrances, particularly in high-volume products. Both types are considered to be within the scope of the present invention.

A pH modifier may be part of the disclosed formulation. A pH modifier is a compound that will adjust the pH of a formulation to a lower, e.g., more acidic pH value, or to a higher, e.g., more basic pH value. The disclosed formulations may contain such pH modifiers as is necessary.

In some embodiments, an SPF enhancer or booster, including styrene/acrylates copolymer (such as Sunspheres PGL, commercially available from Dow Chemical), and/or skin active agents, and/or anti-oxidants, may be optionally added to the formulation.

The disclosed formulation may be used as an After Sun formulation. As used herein, an After Sun emulsion formulation is defined as a formulation that can be administered after a user has been in the sun for any amount of time and is a formulation that provides a soothing or healing effect that is pleasant to the user. Such a formulation can contain, for instance, aloe vera, vitamins A and E, cooling agents, moisturizers, redness-reducing agents and the like.

The present formulation may be used as self-tanning formulation or for sunless tanning. As used herein, the term "sunless-tanning" or "self-tanning formulations" refer to formulations which, when applied to human skin, impart thereto an appearance similar to that achieved by exposing the skin to natural or artificial sunlight. Examples of sunless tanning active agents are described in U.S. Pat. Nos. 6,482, 397, 6,261,541, and 6,231,837. Such sunless tanning compositions typically comprise, in addition to an artificial tanning effective amount of a self-tanning agent, effective amounts of a formulation coloring agent and a cosmetically acceptable carrier adapted for topical application to human skin. The self-tanning agents can also include those formulations generally accepted in the art for application to human skin, and which, when so applied, react therein with amino acids so as to form pigmented products. Such reactions give the skin a brown appearance, similar to the color obtained upon exposing it to sunlight for periods of time sufficient to tan the skin. Suitable self-tanning agents include, without limitation, alpha-hydroxy aldehydes and ketones, glyceraldehyde and related alcohol aldehydes, various indoles, imidazoles and derivatives thereof, and various approved pigmentation agents. Presently preferred herein as self-tanning agents are the alpha-hydroxy aldehydes and ketones. Most preferably, the self-tanning agent is dihydroxyacetone ("DHA"). Other suitable self-tanning agents include, without limitation, methyl glyoxal, glycerol aldehyde, erythrulose, alloxan, 2,3-dihydrox-ysuccindialdehyde, 2,3-dimethoxysuccindialdehyde, 2-amino-3-hydroxy-succindialdehyde and 2-benzylamino-3-hydroxysuccindialdehyde.

The disclosed whipped formulation product has been developed, in part, to offer consumers a unique and better way to apply topical products such as sunscreen and skin creams to themselves and others.

One advantage of the disclosed whipped formulation product is during dispensing the density of the formulation contained within the package drops measurably. The resulting dispensed product represents a whipped product (a foam) of substantial rigidity and body, slow to collapse under ambient and elevated temperature conditions but easy to "break" upon physical manipulation, as for example during rubbing. This allows for a more "controlled" and even dispersal/spreading/distribution of product as compared to the initial "un-whipped" presentation of the formulation.

Another advantage of the disclosed whipped product arises from the ability to contain such a large "dispensed volume" in such a condensed package format. The volume comparison between "straight" (un-whipped) and "whipped" formulation is represented in roughly a 1:5 to 1:6 ratio, allowing for a far more consumer friendly and portable package size/format for such a large volume of dispensed product.

In certain embodiments, the disclosed whipped formulation product can allow for more control of spread over body. In certain embodiments, the disclosed whipped formulation product provides a more rigid "push" providing enhanced tactile response. In certain embodiments, the disclosed whipped formulation product is described as "thicker, creamier, and more volume," "lighter during application." In certain embodiments, the disclosed whipped formulation product allows for more control as to "heaviness" of application. In certain embodiments, the disclosed whipped formulation product provides for faster application due to perceived fast absorption.

In certain embodiments, the disclosed whipped formulation product allows for high levels of product evacuation, particularly for viscous products as compared to traditional non-pressurized emulsion packaging. In certain embodiments, the disclosed whipped formulation product with its pressured system allows for elevated levels of gas to be saturated into formulation, beyond what ambient would normally allow, which can increase whipping potential (lower resulting dispensed densities) and reduce sputtering that can be caused by saturating high levels of gas into formulation but failing to provide adequate pressure to contain the saturated gas. In certain embodiments, the disclosed whipped formulation product results in reduced corrosion potential by separating the formulation from the rigid, pressurized container (if metal) by containing the formulation in the internal bag.

In certain embodiments, the disclosed whipped formulation product can have its whipping agent, pressure, and gas dispersion customized for each formulation. Whereas oil and water emulsions are particularly well suited for specific gases, liquid propellants can provide much larger bubble structures. BOV dispensing mechanism allows for co-blending of the various types of liquid and gas-phase propellant allowing to dispense whipped products without substantially altering temperature or potentially induce a cooling effect due to phase change energy absorption.

The disclosed whipped product is a light and spreadable formulation and thus may be particularly well suited for sensitive or compromised skin applications, such as applying a whipped sunscreen product or a whipped after sun product.

The disclosed whipped product form is designed to dispense a product in a controlled manner by delivering a pressurized, foaming formulation via a dispensing orifice at the touch of a button. The product is dispensed via an actuator that depresses a valve stem into a female aerosol valve. Upon activation, the gas-saturated formulation experiences a drop in pressure as it moves from a pressurized containment system to ambient conditions. This change in pressure allows the saturated gas to rapidly expand, creating bubbles within the formulation, leading to a formulation of reduced density. Formulation customizations allow these bubbles to remain stable for 10 seconds or longer, permitting the user to spread the resulting product onto a surface with enhanced coverage benefits.

Although specific suppliers of commercially available ingredients may be listed herein, it is understood that these products may be available from additional suppliers and that the instant invention is not limited to only that ingredient from the specifically cited supplier. Rather the supplier is being provided as an example of what is commercially available.

Description of certain embodiments of the whipped product

Luxurious whipped product, whipped, spongy, soft, pillowy
No shake whipping
Not runny; stays where you put it
Easy to apply and handle, faster, easier application
More controllable, no drip allows precise placement, convenience of C-Spray but no wet-look. Applying easily to back, not chasing a liquid product, no smear mess but pull product to control application. Can apply multiple dollops to body at one time. Thus can put package down and not have to touch again while rubbing in multiple dollops
Quick rub-out time
Different sensory (drag of product), smoothness
Connect emotionally with application experience
Perception—whipped dries more quickly
After feel—no wetness/drag/tackiness
Coping mechanism: previous product dispenser has loud sound and needs shake before coming out, whipped made convenient/quiet/easy dispose Characterization of the product—brightness, density, bubble size, bubble distribution, surface tension, pH, stability, sheer, dose, sound, drag (skin feel)—low drag, sheen, full bodied, insulation, contact temperature, wetness, slip, sound cue Change in physical properties only, maintains formulation properties with enhanced application benefits, "transforms application but not properties"

May have 5×-10× expansion in density and/or volume

Micro-voids, micro-bubbles, infused, air emulsion, trap gas in structure

Consistent whipped product over life of product—beginning to end

Reduce in dead inventory

Stable, supersaturated nitrous oxide loading, helps to create microbubbles and thus unique structure Can create variable drag experience based on processing
    reduced drag application, increased/better/easier application
    low sheer application for sensitive/damaged skin Create and maintain higher solubility product through containment under elevated pressure (allows constant pressure overtime)

Size of nozzle (sheer rate impact)→sound profile

Sensory Impact

The disclosed formulation product represents the careful culmination of advancements in formulation, processing, and packaging to deliver a rich, creamy, spreadable, lightweight whipped product for consumer application. The disclosed formulation also delivers desired sensory impact to a user.

Sensory impact (such as appearance of the whipped product, sound upon dispensing the product from the can, and impact on the skin of the whipped formulation, etc.) to the user may be evaluated by, for example, trained personnel to determine how product variants are perceived differently by the user, with statistical confidence. Those formulations determined to have desired sensory impact are thus selected. In certain embodiments, the user's senses are highly satisfied by the disclosed formulation after its application on the user.

Two intertwined process variables may contribute to controlling the consumer experience associated with a base formula; gas loading (e.g., nitrous oxide) into the formulation with the active ingredient, which impacts density, spreadability, sound, and physical appearance of product; and pre-gas can pressure, which influences stability of gas emulsion, sound, speed of dispense, sputtering, and "quality" characteristics. Multiple product variants, combining these two process variables, are run and are being physically evaluated. Physical measurements may be made, including CT scans to yield "in can" product profile characterization details; dispensing observations (such as appearance of the whipped product, sound upon dispensing the product from the can, and impact on the skin of the whipped formulation, etc.), and high temperature foam stability; and post-dispensing physical measurements including density, bubble size, and bubble size distribution. Sensory impact (such as appearance, sound, and skin impact) to the user of these multiple product variants may be evaluated by, for example, trained personnel to determine how product variants are perceived differently by the user, with statistical confidence. Some of these tested whipped formulations would have desired sensory impact to the user. For any given product, the following parameters, as well as any other parameters that impact a user's sense(s), may be evaluated.

Appearance: visual compactness, integrity of shape, gloss, hue, intensity, brightness, opacity, whitening, etc.

Sound impact upon dispensing from the can: volume, tone, crackling/popping, sputtering, etc.

Skin Feel: firmness, stickiness, cohesiveness, peaking, wetness, spreadability, coolness, thickness, slipperiness, oiliness, waxiness, greasiness, rubs to absorbency, tautness, roughness, thickness of residue, grittiness, graininess, chalkiness, peeling/flaking, pilling, powdery-ness, plastic/coated, etc.

In certain embodiments, the whipped formulations have desired sensory impact to a user, who may be a human user. In certain embodiments, the formulations have high sensory impact to the user; in certain embodiments, the high sensory impact is characterized by one or more of the following: positive appearance, low sound impact, high integrity of shape, visual compactness, high spreadability, positive skin feel, afterfeel (immediately after application or after a few minutes after application, such as about 10 minutes after) as well as other sensory input perceivable by a user.

The disclosed method allows for tweaking the consumer experience attributes of a whipped formulation in multiple directions, allowing is to deliver "soft and gentle" or "aggressive and greasy," etc., depending on consumer preference. Some of the attributes are: appearance, sound impact, integrity of shape, spreadability, and skin feel. All these, as well as other parameters, may be chosen such that the whipped formulation has the desired attributes.

For appearance, in certain embodiments, the appearance is a well-formed dollop; in other embodiments, such as for Kid's Messy-Loud sunscreen, the product upon dispensing sputters.

For sound impact, in certain embodiments, such as Kid's Messy-Loud sunscreen, the sound impact upon dispensing is obnoxiously loud and disruptive; in other embodiments, the sound impact is as low as possible.

For skin feel, in certain embodiments, such as Baby and Clearly Sheer, the skin feel provided by the formulation is a soft, none greasy-feel experience; in other embodiments, such as sunscreen for sport users who want to feel their sunscreen is working hard and staying with them as they move, the skin feel provided is one or more of greasiness, heaviness, and glossy.

In certain embodiments, the disclosed whipped product dispenses in a light whipped form, infused with tiny bubbles that make the texture of the formulation lighter, smoother and easier to spread across the skin. This texture also makes the formulation feel less greasy and more aesthetically pleasing on hands and skin, leaving a 'sumptuous' feel with a sunscreen during application. This formulation spreads quickly and disappears rapidly as the user rubs the formulation into the skin. Such a formulation may even prevent excess application of the agent and may offer ecological advantages.

In another embodiment, the disclosed whipped product offers an easier, faster, smoother, and less greasy skincare formulation than a traditional formulation.

In certain embodiments, the physical stability of the whipped products obtained may also be characterized by means of these tests: determination of the organoleptic characteristics (e.g., aspect, color, odor), characterization of the texture (e.g., thick, fluid, greasy, non-greasy), and characterization of the spreadability.

In certain embodiments, the disclosed formulation has one or more of the following physical characteristics: a majority of bubbles being of a bubble size of less than 20 µm, high number of bubbles, high bubble density, and high foam stability. In certain embodiments, the disclosed formulations have high foam stability at high temperatures, such as at 25° C. to 37° C., or 37° C. to 50° C.

In certain embodiments, the color of the whipped formulation post-dispensing is white. The whiteness of the whipped lotion may be used as a visual queue for application on skin.

In certain embodiments, the formulation has at least about 60% of the gas bubbles at 100 µm, after the formulation is expelled from the package. In certain embodiments, the formulation has at least about 40% of the gas bubbles at ≤60 µm, after the formulation is expelled from the package.

In certain embodiments, the whipped formulation product is characterized by microdispersion. In certain embodiments, the whipped formulation product is characterized by substantially consistent microvoid.

In certain embodiments, the whipped formulation product is highly emollient. In certain embodiments, the whipped formulation product has about 60% or more of the gas bubbles at 100 µm. In certain other embodiments, the whipped formulation product has about 40% or more of the gas bubbles at 60 µm. The gas bubbles are formed from the gas propellant co-mingled with the formulation prior to filling the formulation into the package.

In certain embodiments, the formulation has one or more of characteristics such as little or no wetness after application, having a collapse time of at least 60 seconds, or structurally stable for at least 30 minutes.

EXAMPLES

For this invention to be better understood, the following examples are set forth. These examples are for purposes of illustration only and are not be construed as limiting the scope of the invention in any manner.

Examples 1-2 relate to a whipped lotion product rather than a whipped gel product. However, much of the whipping process are shared by the two products.

Example 1. Laboratory Manufacturing Process for Whipped Sunscreen Lotion SPF 50

TABLE 1

Concentrate (Base Formulation): Whipped Sunscreen Lotion Concentrate, Batch Size: 1000 g.

| | Concentration (% w/w) | Manufacturing Directions |
|---|---|---|
| Part A Ingredients | | |
| Purified water, USP | 43.77 | Step 1: In a container large enough to |
| Avicel RC-591 | 2.00 | hold the entire batch, add the Water of Part A, with rapid mixing, add the Avicel RC-591 of Part A and mix until free from lumps. |
| Part B Ingredients | | |
| Disodium EDTA | 0.10 | Step 2: Add the ingredients of Part B to |
| Ganex P-904 LC | 0.80 | the batch of Step 1 and mix until |
| Glycerin, USP | 2.50 | dispersed. Begin heating the aqueous |
| Sunspheres PGL | 8.00 | phase to 158-167° F. (70-75° C.) with mixing. |
| Part C Ingredients | | |
| Octocrylene, USP | 8.00 | Step 3: In a separate container, add the |
| Octisalate, USP | 4.50 | ingredients of Part C and heat to 158-167° F. |
| Homosalate, USP | 10.00 | (70-75° C.) with mixing until |
| Dicaprylyl Ether | 2.00 | dissolved. |
| Vitamine E, USP | 0.25 | |
| Avobenzone, USP | 3.00 | Step 4: Add the oil phase of Step 3 to the |
| Oxybenzone, USP | 6.00 | batch of Step 2 and mix until homogenous. |
| Prolipid 141 | 4.50 | Turn off heat and cool to at least 113° F. |
| Lanette 22 (CM) | 2.00 | (45° C.). |
| Cetyl Alcohol, NF | 1.00 | |
| Chlorphenesin | 0.27 | |
| Part D Ingredients | | |
| Sodium Ascorbyl Phosphate | 0.01 | Step 5: Add Part D ingredients to the batch then slowly added the Dry-Flo to the |
| Benzyl Alcohol, NF | 0.90 | batch and mix well. |
| Fragrance | 0.40 | |
| Dry-Flo Pure | 4.00 | |
| Part E Ingredients | | |
| Purified water, USP | Q.S. | Step 6: Q.S. the batch with water of Part E and mix well. Package accordingly. |

TABLE 2

Finished Product (Concentrate + Gas): Whipped Sunscreen Lotion SPF 50 (BOV) (Z16-014), Batch Size: 5 oz. Bag on Valve (BOV) Can

|  | Concentration (% w/w) |
| --- | --- |
| Whipped Sunscreen Lotion Concentrate | 98.10 |
| Nitrous Oxide (1st Gas) | 1.90 |

The following three major steps are involved in manufacturing a whipped product (Finished Product).

1) Pre-mixing step: Co-process of a base formulation (Concentrate) and a 1st Gas.
2) Pre-pressurizing step: Pressurizing of a 2nd gas between a bag and the inside wall of the product package.
3) Packaging step: Packaging the pre-mixed formulation (concentrate+the 1st gas) into the pre-pressurized Bag on Valve (BOV) package.

In certain embodiments, the following steps are involved in manufacturing a whipped product.

1) Concentrate Production Step: The base sunscreen emulsion was processed in accordance with the manufacturing process according to Table 1, and held for the Gas Co-Processing step.
2) Gas Co-Processing Step: The base sunscreen formulation was added to the mixing chamber and a 1st Gas was vigorously co-mingled or dispersed with a high pressure mixing head into the base formulation at 150 psig, and held at pressure until Packaging Step.
3) Pre-pressurizing step: Pressurizing of a 2nd gas between a bag and the inside wall of the Bag on Valve product package to no less than 40 psig.
4) Packaging step: Packaging the pre-mixed formulation (concentrate+the 1st gas) into the pre-pressurized Bag on Valve (BOV) package by injection into the two way valve opening at a pressure of at least 400 psig.

Generally, a blended base formulation (e.g., Y71-159) is transferred into a hopper, pressurized and under a controlled temperature, rate of flow and pressure is transferred into a high shear, continuous-flow, high-pressure "whipping" head, which rapidly mixes the base formulation with a series of infusion gas injector ports which controls the gas pressure and rates of flow with a selection of gases (or gas) to rapidly co-mingle the gas (1st gas) and the base formulation, effectively "dispersing" the gas into the formulation prior to injection into the pre-pressurized Bag on Valve (BOV) package. In addition, the gas-infused formulation is tested for density inline and controlled under pressure and finally injected under pressure into the desired package.

Example 2. Exemplary Lotion Formulations

TABLE 3

|  | Concentration (% w/w) | | | |
| --- | --- | --- | --- | --- |
| Ingredient | Whipped Sunscreen Lotion Concentrates Y71-128 (SPF 30) | Whipped Sunscreen Lotion Concentrates Y71-189 (SPF 30) | Whipped Sunscreen Lotion Concentrates Y71-122 (SPF 50) | Whipped Sunscreen Lotion Concentrates Y71-159 (SPF 50) |
| Avicel RC-591 | 2.00 | 2.00 | 2.00 | 2.00 |
| Disodium EDTA | 0.10 | 0.10 | 0.10 | 0.10 |
| Ganex P-904 LC | 0.80 | 0.80 | 0.80 | 0.80 |
| Glycerin | 2.50 | 2.50 | 2.50 | 2.50 |
| Sunspheres PGL | 8.00 | 8.00 | 8.00 | 8.00 |
| Octocrylene | 8.00 | 8.00 | 4.00 | 8.00 |
| Octisalate, USP | 4.50 | 4.50 | 4.50 | 4.50 |
| Homosalate | 10.00 | 10.00 | 10.00 | 10.00 |
| Dicaprylyl Ether | 2.00 | 2.00 | 2.00 | 2.00 |
| Tocopherol | 0.25 | 0.25 | 0.25 | 0.25 |
| Avobenzone | 3.00 | 3.00 | 3.00 | 3.00 |
| Oxybenzone | — | — | 6.00 | 6.00 |
| Prolioid 141 | 4.50 | 4.50 | 4.50 | 4.50 |
| Lanette 22 (CM) | 2.00 | 2.00 | 2.00 | 2.00 |
| Cetyl Alcohol | 1.00 | 1.00 | 1.00 | 1.00 |
| Chlorphenesin | 0.27 | 0.27 | 0.27 | 0.27 |
| Sodium Ascorbyl Phosphate | 0.01 | 0.01 | 0.01 | 0.01 |
| Benzyl Alcohol | 0.90 | 0.90 | 0.90 | 0.90 |
| Fragrance SZ-1405 MOD 2010 | — | 0.40 | — | 0.40 |
| Citrus Waters SZ28506 | 0.15 | — | 0.15 | — |
| Dry-Flo Pure | 4.00 | 4.00 | 4.00 | 4.00 |
| Water | Q.S. | Q.S. | Q.S. | Q.S. |

Example 3. Other Products Have Been Shown to be Whippable, for Example and Without Limitation Category—Class—Whipped Benefit
Whip Cream—Food—Anti-Abuse
Peanut Butter—Food—Ease of Application
Dessert Topping—Food—Ease of Application
Topical Analgesic—OTC Drug—Improved Absorption
Burn Cream—Medical Device Rx—Reduced Spreadability Pain
Medical Haircare—Hair loss—NDA—Reduced Consumer Complaints—Failure to empty
Medical Haircare—Scalp treatment—OTC Drug-Improved Delivery/Application
Petrolatum Gel—OTC Drug—Ease of Application
Hair Styling Product—Cosmetic—Novel Delivery of Thicker Products
Diaper Rash Prevention—OTC Drug—Novel Delivery of Thicker Products
Tooth Whitener—Cosmetic—Better Coverage
Oral Care—Toothpaste—Cosmetic—Improved Delivery
Anti-Fungal treatment—OTC/Rx Drug—Reduced Spreadability Pain/Improved Absorption
Eye-lid Cleanser—Cosmetic—Novel Delivery
Psoriasis treatment—Medical Device—Reduced Spreadability Pain
Colon-Rectal Treatment—Rx—Improved Drug Delivery and Absorption
Acne treatment—OTC Drug—Novel Delivery
Hand Sanitizer—OTC Drug—Formulation Approach
Natural Deodorant—Cosmetic—Improved Spreadability
Shave Prep—Cosmetic-Novel Delivery of Thicker Products
Wound Care—Medical Device—Novel Delivery of Thicker Products
Self-Tanner—Cosmetic—Improved Delivery
Body Moisturizer—Cosmetic—Novel Delivery of Thicker Products
Lice Treatment—Medical Device/OTC—Novel Delivery of Thicker Products
Hair Depilatory—OTC Drug—Novel Delivery of Thicker Products
Anti-Hemorrhagic—Rx/Device—Formulation Compatibility—Non-Flammability—Surgical Application.

Example 4. Gel Products Can Be Whipped

This example shows the manufacture of whipped products using various gas systems, evaluating the whippability of these whipped products, and monitoring the stability of whipped-foams.

A Sunscreen Gel (SPF 50) was selected as the base formulation (Table 4), and various gases (carbon dioxide, isopentane, isobutane, and nitrous oxide) were examined as potential propellants. All whipped gel products except a whipped gel processed with nitrous oxide were prepared in BOV packages. To mimic the performance of a typical whipped product in a BOV package, the whipped gel made with nitrous oxide was shaken vigorously before dispensing to ensure a fine dispersion of nitrous oxide throughout the gel.

Figure 1:
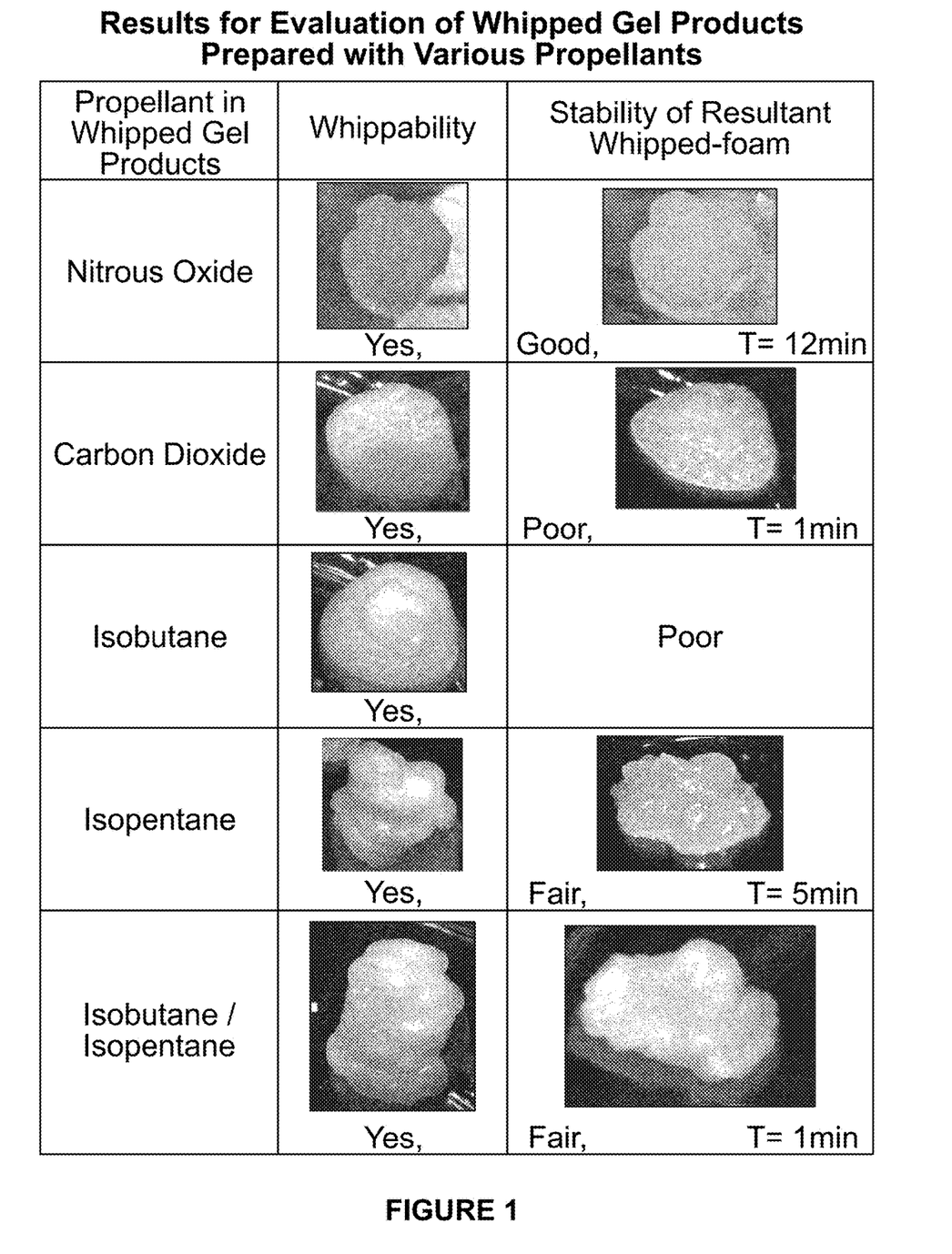
FIG. 1 shows results of whipped gel products prepared with various propellants.

FIG. 1 shows that all the propellants used in this study are capable of producing whippable gel products. The resultant whipped-foams were further evaluated for their stabilities at room temperature (RT). As shown in FIG. 1, whipped-foams dispensed from whipped gel products prepared with carbon dioxide and isobutane were not stable at room temperature. Acceptable "whipped-foam" stability was observed for whipped gel products processed with nitrous oxide, isopentane, and a mixture of isobutane/isopentane.

It is feasible to develop whipped gel products, in which a sunscreen gel formulation is co-processed with, e.g., a nitrous oxide, isopentane, or isobutane/isopentane mixture.

TABLE 4

Ingredient Composition of a Sunscreen Gel SPF 50 (base formulation)

| Ingredient | Concentration (% w/w) |
| --- | --- |
| FlexlThix Polymer | 3.0 |
| R202 Aerosil | 0.7 |
| TM-SI 5 | 1.0 |
| Allianz OPT | 0.5 |
| D C 9701 cosmetic | 2.0 |
| Octocrylene | 9.0 |
| Octisalate | 4.5 |
| Homosalate | 10.0 |
| Dicaprylyl Ether | 5.0 |
| Vitamine E, USP | 0.25 |
| Avobenzone | 3.0 |
| Oxybenzone | 5.0 |
| Dragoxat 89 | 5.0 |
| Wax, white NF | 0.5 |
| Fragrance | 0.1 |
| Alcohol SD 40-B | Q.S. |

TABLE 5

Ingredient Composition of another Sunscreen Gel SPF 50 (base formulation)

| Alcohol SD 40-B | 55.70% |
| --- | --- |
| FlexiThix Polymer | 3.00% |
| Avobenzone, USP | 3.00% |
| Octisalate, USP | 4.50% |
| Octocrylene, USP | 9.00% |
| Oxybenzone, USP | |
| Homosalate, USP | 10.00% |
| TM-Si 5 | 1.00% |
| R202 Aerosil | 0.70% |
| ALLIANZ OPT | 0.50% |
| Dow Corning 9701 Cosmetic Powder | 2.00% |
| Dragoxat 89 (RDI#120076-40) | 5.00% |
| Wax White NF Pellets | 0.50% |
| Dicaprylyl Ether | 5.00% |
| Fragrance SZ-2108 MOD 2010 | 0.10% |
| TOTALS: | 100.00% |

Example 5. Laboratory Manufacturing Process for a Whipped Aqueous Aloe Gel (Finished Product: Z17-057, Concentrate: G59-053)

TABLE 6

Concentrate (Base Formulation): G59-053

| | Concentration (% w/w) | Manufacturing Directions |
|---|---|---|
| Part A Ingredients | | |
| Purified water | 90.8561 | Step 1: In a container large enough to hold the entire batch, add the Water of Part A, with rapid mixing, slowly add Carbopol. |
| Carbopol 980 | 0.65 | |
| Part B Ingredients | | |
| Disodium EDTA | 0.05 | |
| Propylene glycol | 2.13 | Step 2: Add the ingredients of Part B to the batch of Step 1 and mix until dissolved. |
| Glycerin | 2.13 | |
| Germall II | 0.30 | |
| Lidocaine Hydrochloride | 0.532 | |
| Part C Ingredients | | |
| Isopropyl Alcohol, USP | 0.05 | Step 3: Add the ingredients of Part C in order to the batch of Step 2 and mix until dissolved. |
| Dye, Yellow #5, FD&C | 0.0015 | |
| Dye, Blue #1, FD&C | 0.0004 | |
| Aloe Vera Gel 40:1 | 1.25 | |
| Menthol, USP | 0.05 | |
| Polysorbate 80, NF | 0.80 | |
| Part D Ingredients | | |
| Triethanolamine 99% | 1.20 | Step 4: Add Triethanolamine of Part D. Start to cool batch. |
| Part E Ingredients | | |
| Purified water, USP | Q.S. | Step 5: Q.S. the batch with water of Part E and mix well. |

TABLE 7

Finished Product (Concentrate + Propellant): Whipped aqueous aloe gel (BOV) (Z17-057), Batch Size: 5 oz. Bag on Valve (BOV) Can

| Part A Ingredients | Concentration (% w/w) | Manufacturing Directions | |
|---|---|---|---|
| Whipped aqueous aloe gel Concentrate (G59-053) | 98.0 | FILL CANS 98.0/2.0 AS FOLLOWS: | |
| | | % W/W | INGREDIENT |
| Nitrous Oxide | 2.0 | 98.0 | Whipped aqueous aloe gel (G59-053) |
| | | 2.0 | Nitrous Oxide |

Figure 2:
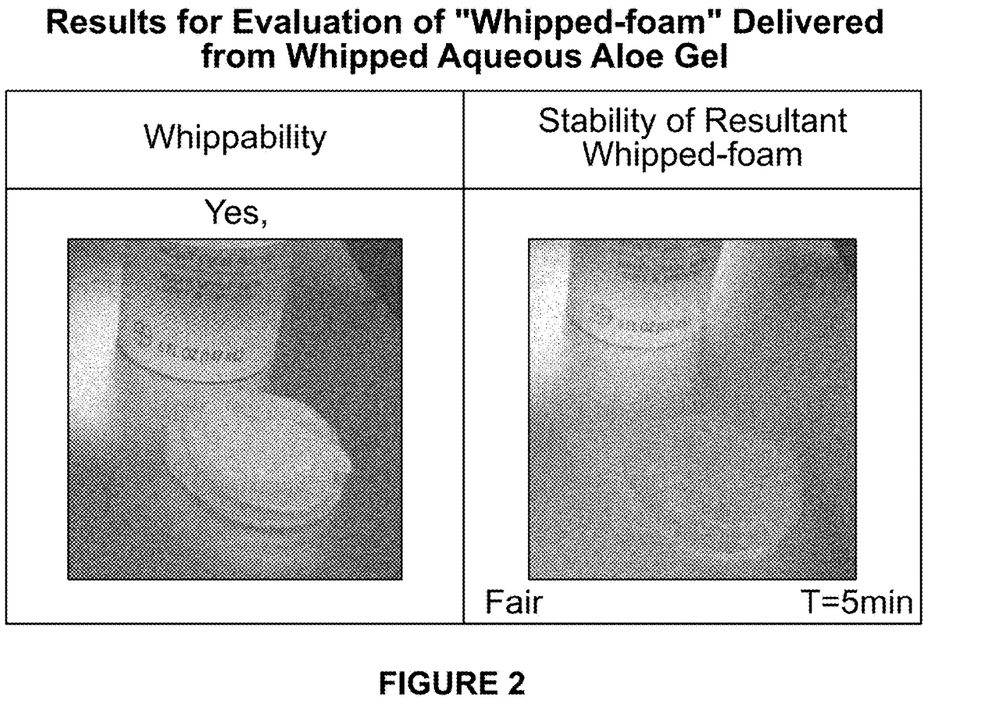
FIG. 2 shows the results for evaluation of "Whipped-foam" Delivered from whipped aqueous aloe gel.

FIG. 2 shows the results for evaluation of "Whipped-foam" Delivered from whipped aqueous aloe gel. The gel is whippable and is fairly stable.

Other Embodiments

The foregoing description discloses only exemplary embodiments of the invention.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the appended claims. Thus, while only certain features of the invention have been illustrated and described, many modifications and changes will occur to those skilled in the art. It is therefore to be understood that the appended claims are intended to cover all such modifications and changes as fall within the true spirit of the invention.

What is claimed is:

1. A stable whipped gel formulation expelled from a pressurized package,
    said formulation comprising a whipping agent and one or more active agents, said whipping agent being dispersed in the formulation,
    and said formulation comprising about 25% to about 60% denatured alcohol,
    one or more film forming agents, including about 1% to about 5% octyldodecyl/glyceryl hydroxy stearate dilinoleate dimethicone copolymer,
    about 0.1% to about 1% of acrylates/$C_{12-22}$ alkylmethacrylate copolymer,
    about 0.1% to about 1% of Beeswax, and
    about 1% to about 5% of polyvinylpyrrolidone,
    one or more viscosity increasing agents, one of which is 0.1% to about 1% of fumed silica,
    one or more skin conditioning agents, and
    one or more emollients, including about 1% to about 10% of ethylhexyl isononanoate and about 1% to about 10% dicaprylyl ether; and
    about 1% to about 5% of dimethicone/vinyl dimethicone crosspolymer;
    wherein said pressurized package is under sufficient pressure suitable to maintain the whipping agent dispersed in the formulation; and
    wherein said pressurized package is under sufficient pressure to expel said formulation as a whipped formulation upon application of external force on said formulation in said package;
    wherein said formulation is a stable anhydrous whipped gel formulation that remains structurally stable for at least 30 minutes after being expelled from said package and has a collapse time of at least 60 seconds; wherein said whipping agent is nitrous oxide, isopentane, or isobutane/isopentane mixture.

2. The gel formulation of claim 1, wherein said package maintains at least a minimal amount of pressure until substantially all the formulation in the package is expelled as a whipped formulation.

3. The gel formulation of claim 1, wherein said package comprises a pressure generating and maintaining component, wherein said component comprises one or more gas and/or liquid propellants which are not co-mingled with the formulation.

4. The gel formulation of claim 1, wherein said formulation is a sunscreen and said active ingredient is a sunscreen active ingredient.

5. The gel formulation of claim 1, wherein said formulation has at least about 60% of the gas bubbles at ≤100 μm, after the formulation is expelled from the package.

6. A pressurized package comprising a stable whipped gel formulation, said formulation comprising a whipping agent co-mingled with one or more active agents, said whipping agent being dispersed in the formulation;

and said formulation comprising about 25% to about 60% denatured alcohol, one or more film forming agents, including about 1% to about 5% octyldodecyl/glyceryl hydroxy stearate dilinoleate dimethicone copolymer, about 0.1% to about 1% of acrylates/$C_{12-22}$ alkylmethacrylate copolymer, about 0.1% to about 1% of Beeswax, and about 1% to about 5% of polyvinylpyrrolidone, one or more viscosity increasing agents, one of which is 0.1% to about 1% of fumed silica, one or more skin conditioning agents, and one or more emollients, including about 1% to about 10% of ethylhexyl isononanoate and about 1% to about 10% dicaprylyl ether; and about 1% to about 5% of dimethicone/vinyl dimethicone crosspolymer;

wherein said pressurized package is under sufficient pressure suitable to maintain the first whipping agent dispersed in the formulation;

wherein said pressurized package is under sufficient pressure to expel said formulation as a whipped formulation upon application of external force on said formulation in said package; and wherein said formulation is an anhydrous stable whipped gel formulation that remains structurally stable for at least 30 minutes after being expelled from said package and has a collapse time of at least 60 seconds; wherein said whipping agent is nitrous oxide, isopentane, or isobutane/isopentane mixture.

7. The package of claim 6, wherein said package maintains at least a minimal amount of pressure until substantially all the formulation in the package is expelled as a whipped formulation.

8. The package of claim 6, wherein said package comprises a pressure generating and maintaining component, wherein said component comprises one or more second gas and/or liquid propellants which are not co-mingled with the formulation.

9. The package of claim 6, wherein said package is a bag on valve (BOV) pressurized assembly, comprising a two-way fill/dispensing valve, an attached internal high barrier bag affixed to said valve, and rigid container adapted to holding positive pressure affixed to the valve.

10. The package of claim 6, wherein said formulation has at least about 60% of the gas bubbles at ≤100 μm, after being expelled from the package.

11. The package of claim 6, wherein the package does not need to be shaken to dispense the formulation.

12. The formulation of claim 1, wherein the package does not need to be shaken to dispense the formulation.

* * * * *